United States Patent [19]

Kurakata

[11] Plant 4,423

[45] Jun. 5, 1979

[54] YELLOW PEACH TREE

[76] Inventor: Eizo Kurakata, 1-14-18, Kamikitazawa, Setagaya-ku, Tokyo, Japan

[21] Appl. No.: 898,285

[22] Filed: Apr. 20, 1978

[30] Foreign Application Priority Data

Oct. 24, 1977 [JP] Japan ..... 52-127193

[51] Int. Cl.[2] ..... A01H 5/03

[52] U.S. Cl. ..... Plt./43

[58] Field of Search ..... Plt./43

*Primary Examiner*—Robert E. Bagwill

*Assistant Examiner*—James R. Feyrer

*Attorney, Agent, or Firm*—Armstrong, Nikaido, Marmelstein & Kubovcik

[57] ABSTRACT

Disclosed herein is a yellow peach tree which has large lanceolate leaves with a slightly swollen margin and rose-pink and largely polliniferous flowers, and which can produce a regular round, clingstone fruit having a sturdy yellow skin partially tinged with red where exposed to sun and having yellow, delicately-textured and slightly sourish-sweet flesh.

3 Drawing Figures

BACKGROUND OF THE VARIETY

The present invention relates to a new and distinct variety of yellow peach tree which has large lanceolate leaves with a slightly swollen margin and rose-pink and heavily polliniferous flowers, and which can produce a regular round, clingstone fruit having a sturdy yellow skin partially tinged with red where exposed to sun and having yellow, delicately-textured and slightly sourish-sweet flesh. The variety of yellow peach tree according to the instant invention is being marketed under the name of "Kurakata Yellow Peach Tree" or "Kurakata Yellow Peach".

For over approximately twenty-five years, I have been engaged in an extensive and continuing yellow peach breeding program in my orchard located at 1-14-18 Kamikitazawa, Setagaya-ku, Tokyo, Japan. The purpose of such program is to provide improved varieties of yellow peach trees which are capable of producing relatively large fruit suitable mainly for eating during the fresh stage even though they can be used for canning.

The instant variety of yellow peach tree was originated by me in my orchard, located at the above-mentioned address, from Tusberta, a female parent (♀), and Ban Kitou, a male parent (♂). The Tusberta of an improved canning grade, was originated by me at Jang Seng-Po, Uelsanshi, Korea, when I lived there in 1940, from the variety, Tuscan, which is an old yellow peach canning grade (in USA), and the variety, Elberta, which is a golden yellow-skinned freestone peach with yellow flesh (in USA). The main botanical properties of the variety, Tusberta, used as a female parent, are as follows.

Tree: Vigorous growing and upright.

Leaves: Lanceolate form with a crenate and swollen margin, which form is different from that of the leaves of Oriental peach varieties.

Flowers: Rose-pink, small flowered, little pollen, and relatively early blooming.

Fruit:

*Size.*—Large; maximum weight—400 g or more; average weight—approximately 350 g.

*Form.*—Round with a small projection at the apex.

*Color.*—Yellow; after ripening, partially tinged with red where exposed to sun and having an extremely beautiful appearance.

*Flesh.*—Yellow clingstone with a delicate texture.

*Taste.*—Normal sugar content with a somewhat strong sourness (or acidity); better taste when eaten fresh than that of the parent, Elberta.

Culture: Many fruits fall when grown in diluvium (volcanic ash soil), but few when grown in clayey soil.

The variety, Ban Kitou, used as the male parent in the breeding of the instant variety, was discovered as a spontaneous seedling variety by me around 1940 at the above-mentioned place in Korea. The main botanical properties of the variety, Ban Kitou, are as follows.

Tree: Ordinary growing.

Leaves: Since no swollen margin appears on the leaves, the Ban Kitou seems to be an Oriental variety.

Flowers: Rose-pink, polliniferous and large flowered.

Fruit:

*Size.*—Medium, no distinct shape.

*Appearance.*—Beautiful; yellow in color and partially tinged with red.

*Flesh.*—Yellow and delicate in texture.

*Taste.*—High sugar content and low sourness. Only sweetness can be tested.

*Ripening period.*—Between the beginning and the middle of August in Tokyo.

(Remarks) This variety is not suitable for canning because it softens upon ripening.

Even since the discovering of the desired variety of yellow peach tree by me in 1960, I have asexually reproduced this variety in my orchard by budding and top-working on young and old established trees of all sizes. It has been confirmed that the characteristics of this new variety are very uniform and stable through succeeding propagations.

SUMMARY OF THE VARIETY

The new variety of yellow peach tree has large lanceolate leaves with a slightly swollen margin which is not as swollen as that of Tusberta; rose-pink and largely polliniferous flowers which are small flowered and self-fertilized; a great amount of fruit which has a sturdy skin, an extremely beautiful appearance, a regular round shape, and a yellow color partially tinged with red where exposed to sun; and flesh which is yellow in color and very delicate in texture with a very small amount of fibers and which has a clingstone, the flesh portions around the stone being of a light color, the taste of the flesh being of a slightly sourish-sweetness and having substantially no difference between the top and the bottom of the fruit, and the flesh having a distinctive good flavor.

BRIEF DESCRIPTION OF THE DRAWING

The accompanying color photographic reproductions show typical specimens of my new variety of the yellow peach tree, wherein.

DESCRIPTION OF THE VARIETY

The botanical characteristics of the new and distinct variety of yellow peach tree are as follows.

Tree:

*Size.*—Medium.
*Vigor.*—Vigorous.
*Production.*—Productive.
*Resistance to diseases.*—Strong.

Trunk:

*Size.*—Medium.

Branches:

*Size.*—Medium.

Figure 1:
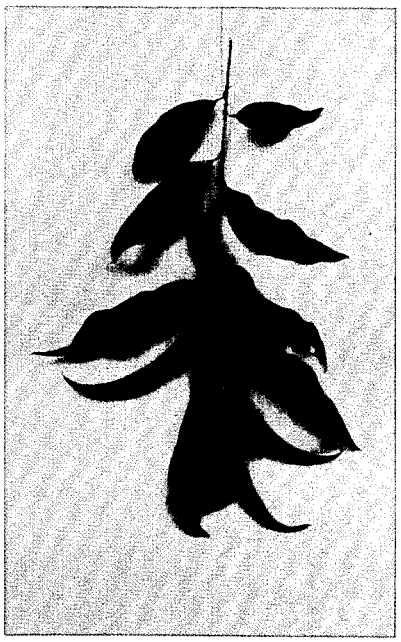
FIG. 1 is a view of a twig with leaves of the new variety of yellow peach tree.

Leaves:

*Size.*—Medium.
*Form.*—Lanceolate, with a crenate margin.
*Color.*—(a) Young (or new) leaves — R.H.S. (Royal Horticultural Society) Color Chart 138/B-D Green Group color. (b) Grown leaves — R.H.S. Color Chart 137/A Green Group color (See FIG. 1).
*Glands.*—Reniform.

Figure 2:
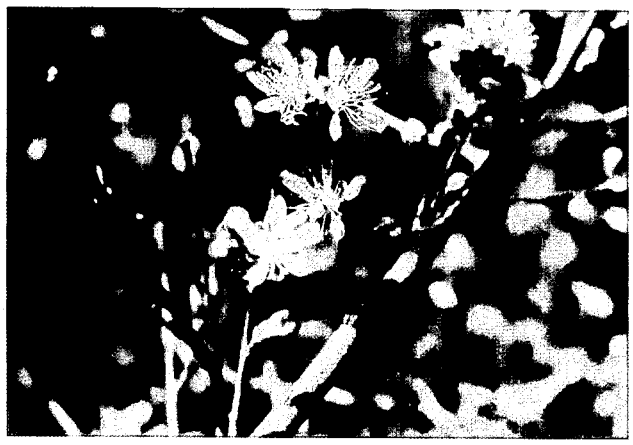
FIG. 2 is a view of the new variety of yellow peach tree in bloom.

Flowers: Tree has many flower buds. Blossoms are of a relatively small size (See FIG. 2). Flowers are small flowered, largely polliniferous and self-fertilized.

*Color.*—Rose-pink.
*Blooming period.*—Around Tokyo, the last eleven days of March through the first ten days of April. Early, as compared with the conventional varieties. Only a few fruits fall even when the tree is grown in volcanic ash soil around Tokyo.

Figure 3:
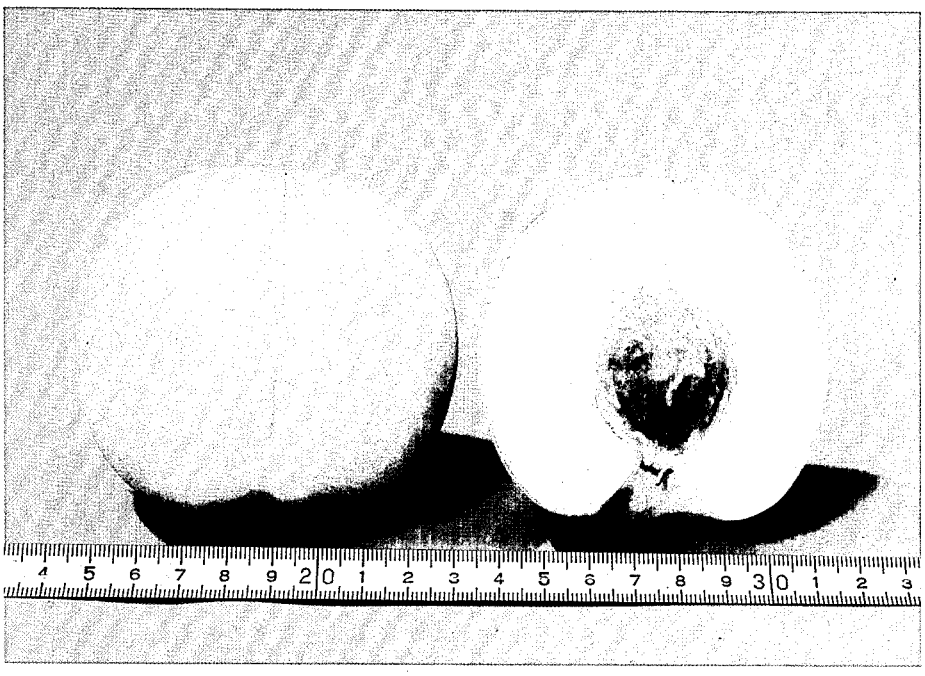
FIG. 3 is a view of a fruit of the new variety, which was grown by wrapping a bag to prevent insect attacks, and a cross-sectional view of a fruit cut in half to expose the flesh with the clingstone.

Fruit:

*Weight.*—220 through 350 g. Average — 250 g.
*Form.*—Uniform, round (or globose) and large in size. Cavity is medium in size in terms of its depth and width. Has a clear suture.
*Skin.*—Medium in thickness and sturdy.
*Maturity.*—Fruit matures from beginning through middle of August. Ripens evenly without ripening first at the top of the fruit. If the fruit is picked during the latter part of its greenish stage and allowed to ripen within a period of, for example, 6 to 8 days, the fruit of the new variety neither exhibits any major changes in its normal ripened appearance nor exhibits any major changes in its taste, contrary to fruits of conventional varieties. Therefore, the new variety can withstand long-distance transportation and is suitable to be sold in a store as a fresh fruit.
*Color of skin.*—R.H.S. Color Chart 19/A Yellow Orange Group color tinged with R.H.S. Color Chart 41/4-47/A Red Group color where skin is exposed to sun (See FIG. 3).
*Color of flesh.*—R.H.S. Color Chart 17/B Yellow Orange Group color (See FIG. 3).
*Flesh.*—Delicately-textured with a large amount of fruit juice and a small amount of fibers.
*Taste.*—Strong sweetness and a little sour. There is no sharpness in taste as compared with that of the conventional varieties of yellow peach tree.
*Stone.*—Clingstone, small in size as compared to those of the conventional varieties.

In addition to the above-mentioned botanical characteristics, data from a detailed examination of the fruit of the new variety are shown below.

Test Method:

*Date of picking.*—Aug. 10, 1977.
*Date of test.*—Aug. 13, 1977.
*Condition when tested.*—Soft ripened state.
*Number of test specimens.*—5.

Test Item:

(1) pH measurement according to glass electrode. The test results are shown in the Table shown below.

(2) Titratable Acidity determined according to the titration by 0.1N NaOH and calculated in terms of malic acid. The test results are shown in Table below.

(3) Sugar Content determined by using an available refraction saccharometer. The results were 12 through 16%.

(4) Soluble Solid Content — 10 g of flesh were sampled and the water content thereof was determined by using an infrared water content analyzer. The result was shown as the weight of the solid content at a constant weight. The average soluble solid content of the samples was 11.0% by weight.

Table

| | Sample No. | | | | | |
|---|---|---|---|---|---|---|
| | 1 | 2 | 3 | 4 | 5 | Average |
| pH | 4.78 | 4.82 | 4.89 | 4.89 | 4.81 | 4.84 |
| Titratable Acidity (Malic Acid g/100ml) | 0.43 | 0.37 | 0.35 | 0.46 | 0.30 | 0.38 |

(Remarks) The tests were conducted with respect to fruit juice of each fruit which was squeezed from about three-quarters of the flesh of the fruit and strained through a cotton gauze.

The new variety of yellow peach tree, as well as the Tusberta variety herein described, is cultivated and kept at my farm located 1-14-18 Kamikitazawa, Setagaya-ku, Tokyo, Japan.

Since the new variety, the so-called "Kurakata Yellow Peach Tree", has a strong resistance to diseases which generally attack peach trees, this variety can be easily cultivated. Since this new variety has largely polliniferous flowers which are self-fertilized, the trees of only this variety can be planted at an orchard or one single tree of this variety can be planted in a home garden. In addition, since only a few fruits fall during their growing period, this variety can be cultivated economically.

When clear bags for preventing insect attacks, such as those made of paraffin paper and the like, are used for wrapping fruits during their growing period, the color of the fruit becomes more beautiful and the red tinge can be easily produced on the surface of the fruit. It has also been found that, if the new variety of the present invention is cultivated without using any bag for preventing insect attacks, no substantial changes with respect to the qualities of the fruit will occur.

What I claim is:

1. A new and distinct variety of yellow peach tree, substantially as illustrated and described herein, characterized over the known yellow peach tree by having large lanceolate leaves with a slightly swollen margin which is not as swollen as that of Tusberta; rose-pink and largely polliniferous flowers which are small flowered and self-fertilized; a great amount of fruit which has a sturdy skin, an extremely beautiful appearance, a regular round shape, and a yellow color partially tinged with red where exposed to sun; and flesh which is yellow in color and very delicate in texture with a very small amount of fibers and which has a clingstone, the flesh portions around the stone being of a light color, the taste of the flesh being of a slightly sourish-sweetness and having substantially no difference between the top and the bottom of the fruit, and the flesh having a distinctive good flavor.

* * * * *